United States Patent [19]

Schaefer et al.

[11] Patent Number: 5,417,960
[45] Date of Patent: May 23, 1995

[54] NITROGEN-CONTAINING CYCLIC LIGANDS, METALLIC COMPLEXES FORMED BY THESE LIGANDS, DIAGNOSTIC COMPOSITIONS CONTAINING THESE COMPLEXES AND PROCESS FOR THE PREPARATION OF THE LIGANDS

[75] Inventors: Nichel Schaefer, Chilly-Mazarin; Didier Doucet, Livry-Gargan; Bruno Bonnemain, Villeparisis; Dominique Meyer, Paris; Dominique Paris, Aulnay-Sous-Bois, all of France

[73] Assignee: Guerbet S.A., Villepinte, France

[21] Appl. No.: 191,461

[22] Filed: Feb. 3, 1994

Related U.S. Application Data

[60] Continuation of Ser. No. 730,050, Jul. 15, 1991, abandoned, which is a division of Ser. No. 421,592, Oct. 16, 1989, Pat. No. 5,049,667, which is a continuation-in-part of Ser. No. 181,056, Apr. 13, 1988, abandoned.

[30] Foreign Application Priority Data

Apr. 14, 1987 [FR] France ............................ 87 05288
Oct. 14, 1988 [FR] France ............................ 88 13585

[51] Int. Cl.⁶ .................... A61B 5/055; A61K 31/555
[52] U.S. Cl. .................... 424/9.363; 514/184; 514/836; 436/173; 540/474
[58] Field of Search ............. 514/836, 184; 424/9, 424/4; 128/653.4, 654; 436/173, 806; 534/16; 540/474

[56] References Cited

U.S. PATENT DOCUMENTS

| | | | |
|---|---|---|---|
| 4,639,365 | 1/1987 | Sherry | 424/9 |
| 4,647,447 | 3/1987 | Gries et al. | 424/9 |
| 4,877,600 | 10/1989 | Bonnemain et al. | 424/4 |
| 4,885,363 | 12/1989 | Tweedle et al. | 540/465 |
| 4,985,233 | 1/1991 | Klaveness et al. | 424/9 |
| 5,198,208 | 3/1993 | Berg et al. | 424/1.1 |

FOREIGN PATENT DOCUMENTS 202869A 3/1984 Japan .

OTHER PUBLICATIONS

Deutsch, J et al., Chem. Abstracts 111:208180b (1989).
Deutsch, J et al., Chem. Abstracts 112:135602z (1989).

*Primary Examiner*—Gary E. Hollinden
*Attorney, Agent, or Firm*—Jacobson, Price, Holman & Stern

[57] ABSTRACT

The subject of the invention is nitrogen-containing cyclic ligands and metal complexes formed by these ligands, the uses of these complexes as magnetic resonance imaging (MRI) agents, as X-ray contrast agents and as chemical shift reagents in vivo.

33 Claims, No Drawings

NITROGEN-CONTAINING CYCLIC LIGANDS, METALLIC COMPLEXES FORMED BY THESE LIGANDS, DIAGNOSTIC COMPOSITIONS CONTAINING THESE COMPLEXES AND PROCESS FOR THE PREPARATION OF THE LIGANDS

This application is a continuation of U.S. application Ser. No. 07/730,050 filed Jul. 15, 1991 abandoned, which is a divisional of Ser. No. 07/421,592, filed Oct. 16, 1989, U.S. Pat. No. 5,049,667 which is a continuation-in-part of Ser. No. 07/181,056 filed Apr. 13, 1988, abandoned.

The present application is a continuation-in-part of application Ser. No. 181 056 filed Apr. 13, 1988.

The present invention relates to new nitrogen-containing cyclic ligands and metallic complexes formed by these ligands, the uses of these complexes as magnetic resonance imaging agents, as X-ray contrast agents and as chemical shift reagents in vivo.

The invention also relates to a process for the preparation of the ligands.

Thus, the invention relates to a ligand having the formula:

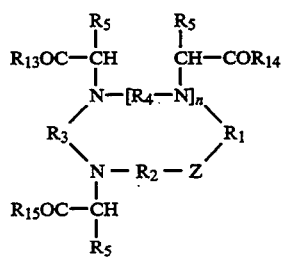

(I)

in which $R_1$ represents a radical of the formula:

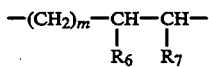

$R_6$ being selected from the group consisting of $C_1$-$C_8$ alkyl, $C_1$-$C_6$ hydroxyalkyl and $C_1$-$C_6$ polyhydroxyalkyl and a group of the formula:

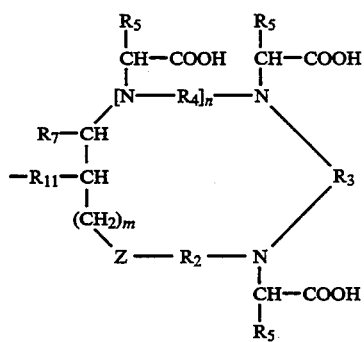

$R_{11}$ being selected from the group consisting of the group A and the groups of the formula:

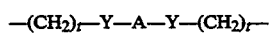

A being selected from the group consisting of $C_1$-$C_8$ alkylene, $C_1$-$C_8$ hydroxyalkylene and $C_1$-$C_8$ polyhydroxyalkylene, Y being selected from

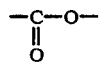

and —O— and t=1 to 4, $R_7$ being selected from the group consisting of hydrogen, $C_1$-$C_{14}$ alkyl, $C_1$-$C_6$ hydroxyalkyl and $C_1$-$C_6$ polyhydroxyalkyl, m=0 or 1

$R_2$, $R_3$, $R_4$, identical or different represent a radical of the formula

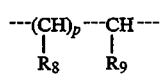

$R_8$ and $R_9$, identical or different, being selected from hydrogen, $C_1$-$C_{14}$ alkyl, $C_1$-$C_6$ hydroxyalkyl and $C_1$-$C_6$ polyhydroxyalkyl, p=1 or 2 n=0, 1 or 2 and $R_5$ is selected from the group consisting of hydrogen, $C_1$-$C_{14}$, alkyl, a $C_1$-$C_6$ hydroxyalkyl and $C_1$-$C_6$ polyhydroxyalkyl, and Z is selected from the group consisting of oxygen and a group of the formula:

$R_{10}$ being selected from the group consisting of hydrogen, $C_1$-$C_{14}$ alkyl, $C_1$-$C_4$ hydroxyalkyl, $C_1$-$C_4$ polyhydroxyalkyl, a group of the formula

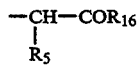

$R_5$ having the meaning given previously, and a group of the formula:

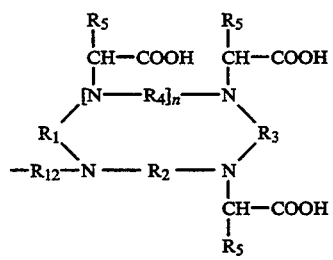

$R_{12}$ being selected from the group consisting of $C_1$-$C_8$ alkylene, $C_1$-$C_8$ hydroxyalkylene and $C_1$-$C_8$ polyhydroxyalkylene, $R_{13}$, $R_{14}$, $R_{15}$ and $R_{16}$, identical or different being selected from the group consisting of hydroxy and a group of the formula

$R_{17}$ and $R_{18}$, identical or different being selected from the group consisting of hydrogen, $C_1$-$C_{14}$ alkyl, $C_1$-$C_6$ hydroxyalkyl and $C_1$-$C_6$ polyhydroxyalkyl, as well as salts thereof.

A preferred group of ligands of the formula I is the ligands having the formula:

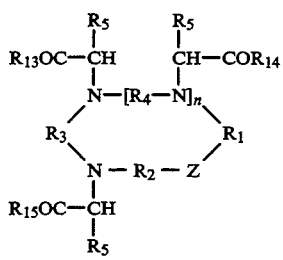

(I)

in which $R_1$ represents a radical of the formula:

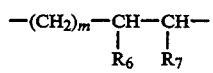

$R_6$ being selected from the group consisting of $C_1$-$C_{18}$ alkyl, $C_1$-$C_6$ hydroxyalkyl, $C_1$-$C_6$ polyhydroxyalkyl and a group of the formula:

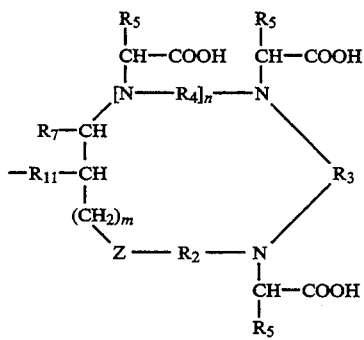

$R_{11}$ being selected from the group consisting of $C_1$-$C_8$ alkylene, $R_7$ being selected from the group consisting of hydrogen, $C_1$-$C_{14}$ alkyl, $C_1$-$C_6$ hydroxyalkyl and $C_1$-$C_6$ polyhydroxyalkyl, m=0 or 1, $R_2$, $R_3$, $R_4$, identical or different represent a radical of the formula

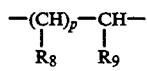

$R_8$ and $R_9$, identical or different, being selected from hydrogen, $C_1$-$C_{14}$ alkyl, $C_1$-$C_6$ hydroxyalkyl and $C_1$-$C_6$ polyhydroxyalkyl, p=1 or 2, n=0, 1 or 2 and $R_5$ is selected from the group consisting of hydrogen, $C_1$-$C_4$ alkyl, $C_1$-$C_6$ hydroxyalkyl and $C_1$-$C_6$ polyhydroxyalkyl, and Z is selected from the group consisting of oxygen and a group of the formula:

$R_{10}$ being selected from the group consisting of hydrogen, $C_1$-$C_{14}$ alkyl, $C_1$-$C_6$ hydroxyalkyl, $C_1$-$C_4$ polyhydroxyalkyl, a group of the formula

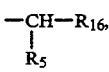

$R_5$ having the meaning given previously $R_{13}$, $R_{14}$, $R_{15}$ and $R_{16}$, identical or different being selected from the group consisting of hydroxy and a group of the formula

$R_{17}$ and $R_{18}$, identical or different being selected from the group consisting of hydrogen, $C_1$-$C_{14}$ alkyl, $C_1$-$C_6$ hydroxyalkyl and $C_1$-$C_6$ polyhydroxyalkyl, as well as salts thereof.

A most preferred group of ligands of the formula is the ligands having the formula:

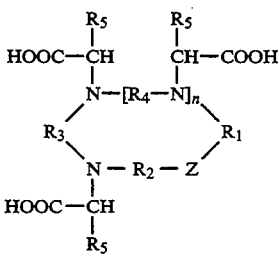

Ia in which $R_1$ represents a radical of the formula:

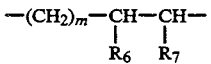

$R_6$ being selected from the group consisting of $C_1$-$C_{14}$ alkyl, $C_1$-$C_4$ hydroxyalkyl, $C_1$-$C_4$ polyhydroxyalkyl and a group of the formula:

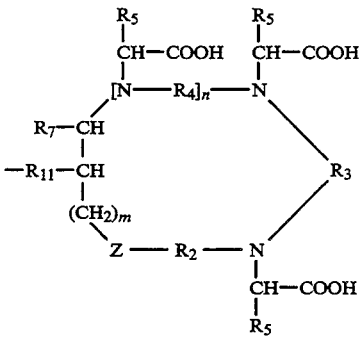

$R_{11}$ being selected from the group consisting of $C_1$–$C_8$ alkylene, $R_7$ being selected from the group consisting of hydrogen, $C_1$–$C_{14}$ alkyl, $C_1$–$C_4$ polyhydroxyalkyl, m=0 or 1, $R_2$, $R_3$, $R_4$, identical or different a radical of the formula

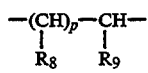

$R_8$ and $R_9$, identical or different, being selected from hydrogen, $C_1$–$C_{14}$ alkyl, $C_1$–$C_{14}$ hydroxyalkyl and $C_1$–$C_{14}$ polyhydroxyalkyl, p=1 or 2, n=0, 1 or 2 and $R_5$ is selected from the group consisting of hydrogen, $C_1$–$C_{4()}$ alkyl, (a) $C_1$–$C_4$ hydroxyalkyl and $C_1$–$C_4$ polyhydroxyalkyl, and Z is selected from the group consisting of oxygen and a group of the formula:

$R_{10}$ being selected from the group consisting of hydrogen, $C_1$–$C_{14}$ alkyl, $C_1$–$C_4$ hydroxyalkyl and $C_1$–$C_4$ polyhydroxyalkyl, a group of the formula

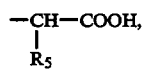

$R_5$ having the meaning given previously, and a group of the formula:

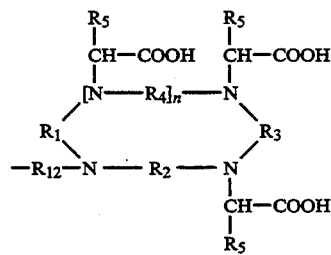

$R_{12}$ being selected from the group consisting of $C_1$–$C_8$ alkylene, $C_1$–$C_8$ hydroxyalkylene and $C_1$–$C_8$ polyhydroxyalkylene, as well as the salts thereof.

The ligands of formula I in which $R_{13}$, $R_{14}$, $R_{15}$ and $R_{16}$ are hydroxy can be prepared by reaction of a compound of formula:

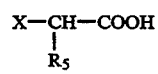   (II)

in which $R_5$ has the meaning given above and X represents a labile group such as chlorine, bromine or iodine atom or a tosyloxy group or a mesyloxy group, with a cyclic amine of the formula:

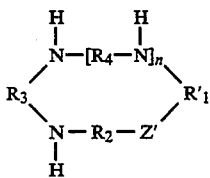   (III)

in which $R_2$, $R_3$, $R_4$, and n have the meanings given above, $R'_1$ represents a radical of the formula:

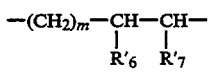

$R'_6$ being selected from the group consisting of $C_1$–$C_{18}$ alkyl, $C_1$–$C_6$ hydroxyalkyl, $C_1$–$C_6$ polyhydroxyalkyl and a group of the formula:

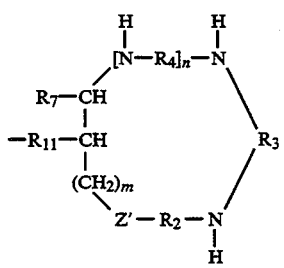

$R_2$, $R_3$, $R_4$, $R_7$, $R_{11}$, m, n, having the meanings given above and Z' is chosen from among an oxygen atom and a group of formula:

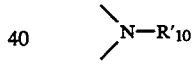

$R'_{10}$ being selected from the group consisting of hydrogen, $C_1$–$C_{14}$ alkyl, $C_1$–$C_4$ hydroxyalkyl, $C_1$–$C_4$ polyhydroxyalkyl, and a group of the formula:

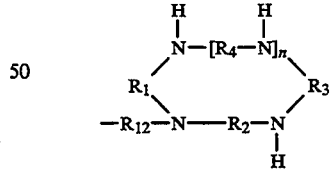

$R_1$, $R_2$, $R_3$, $R_4$, $R_{12}$ and n having the meanings given above.

The ligands of formula I can also be prepared according to a Strecker reaction, by reaction of a cyclic amine of formula III with an aldehyde of formula:

   IIa in which $R_5$ has the meaning given previously, in the presence of hydrogen cyanide or more usually cyanide ions (KCN, NaCN).

The compounds of formula III in which Z' is a group:

can be prepared
a) by reaction of a polyamine of formula:

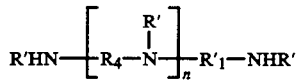

IV in which n, $R_1$ and $R_4$ have the meanings given previously and R' represents a tosyl, mesyl or benzene sulfonyl group, with a compound of formula:

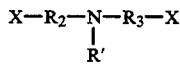

V in which $R_2$, $R_3$ and R' have the meanings given previously and X represents a labile group such as a tosyloxy or mesyloxy group or a chlorine or bromine or iodine atom, or b) by reaction of a diamine of formula:

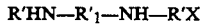

in which $R'_1$ and R' have the meanings indicated previously, with a compound of formula:

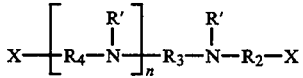

XI

This cyclisation reaction is carried out advantageously in the presence of a phase transfer catalyst.

The polyamines of formula IV can be obtained from dihydroxylamines according to the following scheme:

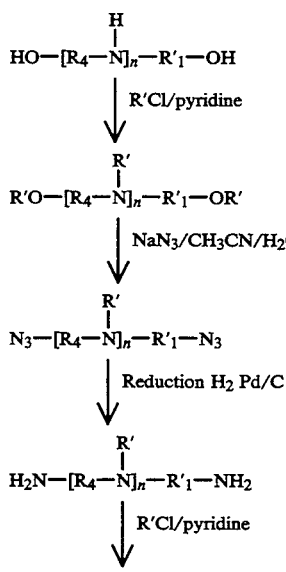

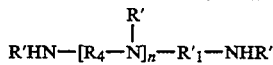

IV

As an alternative, phthalimide is made to react with the compounds of formula VII and hydrazinolysis is carried out in order to convert the compounds of formula VII into the compounds of formula IX.

The compounds of formula III containing 2 nitrogen-containing rings can be prepared according to the procedures specified previously.

Thus, it is possible to react a polyamine of the formula:

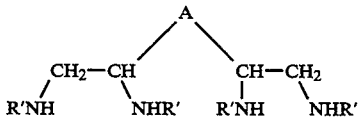

XII in which A and R' have the meanings given previously, with a compound of formula XI in order to obtain a compound of formula III in which $R_{11}$ is a group A.

The polyamine of formula XII can be prepared from a tetrahalogenated derivative by nucleophilic substitution in the presence of sodium azide followed by a reduction in the presence of hydrogen and palladium on charcoal.

As an alternative, the compounds of formula I composed of 2 nitrogen-containing rings and in which $R_{11}$ is a group A, can be prepared by condensation of a compound of formula:

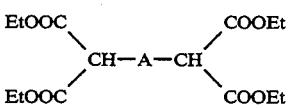

XIII with a polyamine of formula:

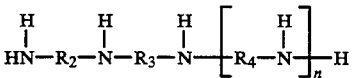

XIV followed by reduction with diborane according to a procedure described by Tabushi et al. (Tetra Letters 12, 1049, 1977).

The compounds of formula I composed of 2 nitrogen-containing rings are then prepared from compounds of formula III with 2 rings as described previously.

As an alternative, compounds of formula I composed of 2 nitrogen-containing rings can be prepared by condensation of a compound of formula I in which $R_1$ is a radical of formula:

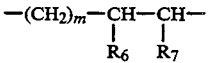

VIII in which $R_6$ is a hydroalkyl group, with an activatable bifunctional compound of formula:

$X_1$ being a COOH group, a COCl group or an acid anhydride.

The compounds of formula I exhibiting 2 nitrogen-containing rings can also be prepared by condensation of a compound of formula:

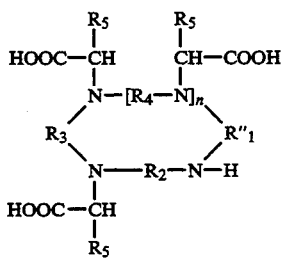 XV in which R''₁ is a radical of formula:

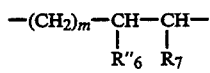

m and R₇ having the meanings given previously and R''₆ being selected from the group consisting of $C_1$–$C_{14}$ alkyl, $C_1$–$C_4$ hydroxyalkyl and $C_1$–$C_4$ polyhydroxyalkyl, with a compound of formula:

 XVI

X having the meaning given previously and R'₁₂ representing a possibly protected R₁₂ group.

Thus are obtained compounds of the formula:

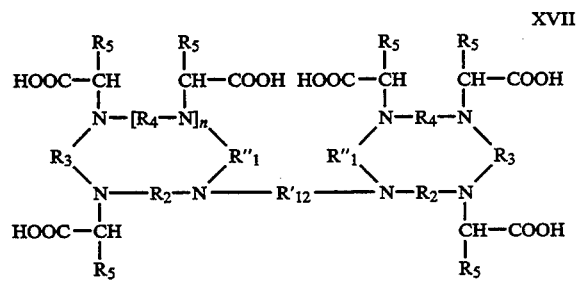 XVII

In addition, the present invention relates to complexes formed by ligands of formula I with metal ions chosen form among the lanthanide ions with atomic numbers 57 to 71, transition metal ions with atomic numbers 21 to 29, in particular $Mn^{2+}$, $Fe^{3+}$ and $Cr^{3+}$, and metal ions with atomic numbers 55, 56, 82 and 83, as well as the salts of these complexes with pharmaceutically acceptable mineral or organic bases or basic amino acids.

Another group of preferred ligands of formula I is the ligands having the formula:

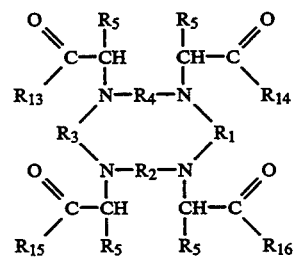 Ib in which

R₁ represents a radical of the formula:

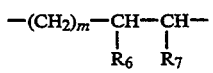

R₆ being selected from the group consisting of $C_1$–$C_{18}$ alkyl, $C_1$–$C_6$ hydroxyalkyl and $C_1$–$C_6$ polyhydroxyalkyl, R₇ being selected from the group consisting of hydrogen, $C_1$–$C_{14}$ alkyl, $C_1$–$C_6$ hydroxyalkyl and $C_1$–$C_6$ polyhydroxyalkyl, m=0 or 1

R₂, R₃, R₄, identical or different represent a radical of the formula

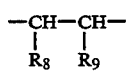

R₈ and R₉, identical or different, being selected from hydrogen, $C_1$–$C_{14}$ alkyl, $C_1$–$C_6$ hydroxyalkyl and $C_1$–$C_6$ polyhydroxyalkyl, R₅ is selected from the group consisting of hydrogen, $C_1$–$C_{14}$, alkyl, $C_1$–$C_6$ hydroxyalkyl and $C_1$–$C_6$ polyhydroxyalkyl, and R₁₃, R₁₄, R₁₅, R₁₆ identical or different being selected from the group consisting of hydroxy and a group of the formula

R₁₇ and R₁₈, identical or different, being selected from the group consisting of hydrogen, $C_1$–$C_{14}$ alkyl, $C_1$–$C_6$ hydroxyalkyl and $C_1$–$C_6$ polyhydroxyalkyl, at least one group R₁₃, R₁₄, R₁₅ and R₁₆ being a group of the formula

as well as salts thereof.

The ligands of formula Ib can be prepared by the reaction of a compound of the formula:

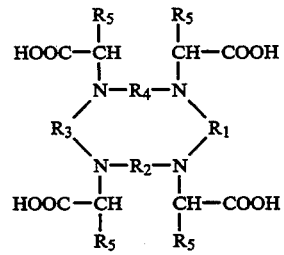 (XVIII)

in which R₁, R₂, R₃, R₄ and R₅ have the meaning given above, with an amine of the formula:

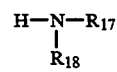 (XIX)

R₁₇ and R₁₈ having the meanings given above.

The reaction may be in particular carried out in the presence of a coupling reactant such as those used for the peptide synthesis and possibly in the presence of catalysts such as pyridine derivatives.

In addition, the present invention relates to complexes formed by ligands of formula I with metal ions chosen from among the lanthanide ions with atomic numbers 57 to 71, transition metal ions with atomic numbers 21 to 29, in particular $Mn^{2+}$, $Fe^{3+}$ and $Cr^{3+}$, and metal ions with atomic numbers 55, 56, 82 and 83, as well as the salts of these complexes with pharmaceutically acceptable mineral or organic bases or basic amino acids.

In such complexes, the metal ions are preferably lanthanides ions selected from gadolinium, europium and dysprosium and ions of transition metals selected from iron ($Fe^{3+}$), manganese ($Mn^{2+}$) and chromium.

As examples of salts mention may be made of those formed with sodium hydroxide, N-methylglucamine, diethanolamine, lysine and arginine.

The complexes can be prepared by reaction of ligands with a metal salt or metal oxide in an aqueous solvent and possibly neutralisation in order to form a salt.

It should be evident that the present invention includes not only the ligands of formula I and the complexes previously defined in the form of racemic mixtures but also the stereoisomers of these ligands and complexes.

The complexes according to the invention can, in addition, be attached to a macromolecule which can become bound preferentially to an organ. Thus, the complexes according to the invention can be linked to proteins and in particular to antibodies.

In addition, they may also be grafted or encapsulated, particularly in liposomes.

The complexes according to the invention formed by the ligands of formula I with paramagnetic ions and their salts with pharmaceutically accepted bases can be used as magnetic resonance imaging agents and particularly with dysprosium as chemical shift reagents in vivo.

The complexes according to the invention formed by ligands of formula I with lanthanide ions of atomic numbers 57 to 71 or ions of metals with atomic numbers 55, 56, 82 and 83 and their salts with pharmaceutically acceptable bases can be used as X-ray contrast agents. For this purpose, the complexes formed with the following metal ions are particularly preferred: Gd, Er, Dy, Tb, Ce, La, Ba and Cs.

Consequently, the present invention relates also to diagnostic composition which can be administered to man, comprising at least one complex formed by a ligand of formula I with metal ions selected from the lanthanide ions with atomic numbers 57 to 71, the transition metal ions with atomic numbers 21 to 29 and the metal ions with atomic numbers 55, 56, 82 and 83, as well as the salts of these complexes with pharmaceutically acceptable mineral or organic bases, or with basic amino acids.

These compositions can be constituted in particular by solutions of a complex according to the invention in a physiologically acceptable aqueous solvent.

The diagnostic compositions according to the invention may be administered:
  by the parenteral route including the intravenous route, the intra-arterial route, the intra-lymphatic route, the sub-cutaneous route
  by the oral route,
  by the sub-arachnoid route,
  by the intrabronchial route in the form of an aerosol,
  by the intraarticular route, locally for the visualisation of cavities (for example, the uterus) in imaging by magnetic resonance, the doses are very variable depending on the routes of administration.

For the intravenous or intra-arterial route, the dose is about 0.01 to 2 mM/kg.

For the oral route, this dose may be as much as 10 mM/kg.

For the other routes of administration, the doses used are usually lower than 1 mM/kg and for the sub-arachnoid route it is usually even lower than 0.05 mM/kg.

The doses are the same for their utilisation as chemical shift reagents in vivo and as contrasting agents in radiology using X rays, except by the intravenous or intra-arterial routes where the doses may be higher than or equal to 5 mM/kg.

In addition, the complexes according to the invention formed by the ligands of formula I with radioactive ions as well as their salts with pharmaceutically acceptable bases can be used as diagnostic agents or therapeutic agents in nuclear medicine. Examples of radioactive ions are radioisotopes of elements such as copper, cobalt, gallium, germanium, indium and, above all, technetium(Tc 99 m).

The following examples illustrate the preparation of the compounds according to present application.

In these examples:
  the NMR spectra were carried out on a Varian EM 360 machine at 60 MHz with TMs as internal reference. Unless otherwise indicated the solvent is $CDCl_3$.
  The IR spectra were carried out on a Perkins-Elmer 1320 apparatus. The spectra of the solids were recorded in the form of KBr disks. In the case of liquids (oils) they were recorded in the absence of solvent.
  The term "buffer" used in thin layer chromatography designates a mixture of 1.5M $NH_4OH$ and 1.5M $(NH_4)_2CO_3$.
  The melting points were measured on a Kofler block.
  The terms used relating to analyses during complexation: "absence of free $Gd^{3+}$ and of free ligands" are to be understood within the limits of detection of the methods used, i.e. <4 ppm and <5 ppm for $Gd^{3+}$ and ligand, respectively.

EXAMPLE I: Preparation of 2,6-dimethyl-1,4,7,10-tetraazacyclododecane-N,N',N'',N'''-tetraacetic acid a) Preparation of N-tosyl-bis (2-tosyloxy propyl) amine.

A solution of 53.2 g (0.4 mole) of diiso-propanolamine in 50 cm³ of pyridine is added dropwise with cooling to a solution of 248 g (1.3 mole) of tosyl chloride in 200 cm³ of pyridine at 0° C. so that the temperature is maintained between 0° and 5° C. The mixture is left at this temperature for 72 h. It is then poured into 2 l of water plus ice and 250 cm³ of concentrated hydrochloric acid.

The tosylated derivative is extracted with 2 l of methylene chloride. The organic phase is dried over sodium sulphate, filtered then decolourised with 3 SA charcoal and refiltered through a bed of silica. After evaporation of the salt 193.8 g of a yellow oil remain (yield 81%; Rf=0.7 silica/$CH_2Cl_2$/acetone/98/2) which is used in the next step without purification.

$^1$HMNR spectrum: 6H $CH_3$ (doublet 1.2 and 1.3 ppm); 9H $CH_3$ tosyl (singlet 2.5 ppm); 4H $CH_2$ (multiplet centred on 3.3 ppm); 2H CH (quadruplet between 4.7 and 5.1 ppm); 12H aromatics (multiplet 7.3 and 8 ppm).

b) Preparation of N-tosyl-bis(2-azido propyl) amine.

To 193.8 g (0.32 mole) of the compound obtained in a in 1.2 l of acetonitrile and 300 cm³ of water are added 65.1 g of sodium azide (1 mole). The mixture is stirred and heated at 75° C. for 48 h. After cooling, the acetonitrile is evaporated in a vacuum.

The residue is taken up in 1 l of methylene chloride. The organic phase is washed with water, dried and filtered through a bed of silica (200 g). After evaporation 82 g of a clear yellow oil remain (yield 75%, Rf=0.85 silica $CH_2Cl_2$/acetone/92/2) sufficiently pure to be used directly.

IR spectrum $N_3$=2100 cm$^{-1}$ intense.

c) Preparation of N-tosyl-bis(2-amino propyl)amine.

82.2 g (0.244 mole) of the compound obtained in b are dissolved in 500 cm³ of ethanol containing 8 g of 5% palladium on charcoal at 50% humidity.

The mixture is stirred vigorously while a gentle stream of hydrogen is passed through (evacuation of nitrogen which is released). After 8 h at ambient temperature, TLC shows the absence of the azide function. The mixture is then filtered and evaporated. 68.4 g of a clear yellow oil are obtained (yield 98.5%; Rf=0.6 silica/MeOH/$NH_4OH$.95/5) which is used without purification.

NMR spectrum: 6H $CH_3$ (doublet 0.9 and 1 ppm); 3H $CH_3$ tosyl (singlet at 2.4 ppm); 6H $CH_2$ and CH (complex multiplet between 2.7 and 3.2 ppm); 4H aromatics (multiplet between 7.1 and 7.7 ppm).

d) Preparation of N-tosyl-bis[(tosylamino)propyl]amine.

93 g (0.5 mole) of tosyl chloride are added in portions to 68.4 g (0.24 mole) of the amine obtained in c in 500 cm³ of methylene chloride and 70 cm³ (0.5 mole) of triethylamine at 0° C. After the addition is complete, the mixture is stirred for 6 h at ambient temperature. The reaction mixture is then washed with 600 cm³ of water, the organic phase is dried, evaporated to dryness and the residue is chromatographed on a column of silica with pure methylene chloride, then with a methylene chloride/methanol/98/2 mixture. The fractions of interest are evaporated and the solid residue is recrystallised from ethanol. After filtration and drying the mass obtained is 99.1 g (yield 70%).

NMR spectrum: 6H $CH_3$ (doublet 0.9, 1 ppm); 9H $CH_3$ p-tosyl (singlet 2.4 ppm); 4H $CH_2$ (triplet centred on 2.9 ppm); 2H CH (doublet 3.3 and 3.5 ppm); 12H aromatics (multiplet centred on 7.4 ppm).

e) Preparation of N-tosyl-bis(2-tosyloxyethyl)amine.

A solution of 32.5 g (0.31 mole) of diethanolamine in 60 cm³ of pyridine are added slowly to a solution of 185 g (0.97 mole) of tosyl chloride in 220 cm³ of pyridine at 0° C. so that the temperature does not exceed 5° C. After the addition is complete, the mixture is maintained at this temperature for 1 h, then it is poured into 220 cm³ of ice-cold water with vigorous stirring. After filtration, washing and drying 148.4 g of precipitate are obtained (yield 85%; Rf=0.6 silica/$CH_2Cl_2$/acetone/98/2).

NMR spectrum: 9H $CH_3$ tosyl (singlet 2.4 ppm); 4H $CH_2N$ (triplet at 3.4 ppm); 4H $CH_2$ (triplet at 4.1 ppm); 12H aromatics (multiplet between 7.1 and 7.7 ppm).

f) Preparation of N,N',N'',N'''-tetratosyl-2,6-dimethyl-1,4,7,10-tetraazacyclododecane 65 g (0.11 mole) of the compound obtained in d dissolved in 500 cm³ of dry DMF are added dropwise to 8.8 g (0.22 mole) of a 60% suspension of NaH in oil in 50 cm³ of DMF. The addition is carried out at ambient temperature and in such a manner that there is a steady release of hydrogen. After the addition is complete, the mixture is heated to 100° C. and a solution of 68.1 g (0.12 mole) of the compound obtained in e dissolved in 500 cm³ of dry DMF are added dropwise. The reaction mixture is then maintained at this temperature for 24 h with vigorous stirring.

The solvent is then evaporated in a vacuum and the residue is taken up in a $CH_2Cl_2/H_2O$ mixture. The organic phase is washed with water, dried and evaporated to dryness. The residue (100 g) is recrystallised from isopropanol, then from toluene to give, after filtration, washing with isopropyl ether and drying, 36 g of a white solid (yield 40%; Rf=0.5–0.6 silica/$CH_2Cl_2$/acetone/98/2).

NMR spectrum: 6H $CH_3$ (doublet at 1 and 1.2 ppm); 12H $CH_3$ tosyl (singlet 2.4 ppm); 14H $CH_2$ and CH (multiplet between 3 and 4.5 ppm); 16H aromatics (multiplet between 7.1 and 7.7 ppm).

g) Preparation of N,N',N'',N'''-tetratosyl-2,6-dimethyl-1,4,7,10-tetraazacyclododecane (variant).

A freshly prepared solution of sodium ethylate (60 mmoles) in 200 cm³ of dry DMF is added rapidly to a solution of 17 g (28.7 mmoles) of the compound obtained in d in 100 cm³ of ethanol at reflux. The mixture obtained becomes clear and is refluxed for 1–2 h. The solvents are then evaporated to dryness, the residue is taken off in 200 cm³ of DMF and heated to 100° C. A solution of 17 g (30 mmoles) of the compound obtained in e in 100 cm³ of DMF is added to this solution during ½ h. The reaction mixture is maintained at 100° C. overnight. The DMF is then evaporated and the residue is taken up in a $H_2O/CH_2Cl_2$ mixture. The product derived from the organic phase is chromatographed on a column of silica with the mixture $CH_2Cl_2$/ethyl acetate/98/2 as eluant. The product is recrystallised from isopropyl ether and weighs 13.5 g after drying (yield 58%; Rf=0.5–0.6 silica/$CH_2Cl_2$/acetone/98/2).

Spectrum identical with that obtained in f.

h) Preparation of 2,6-dimethyl-1,4,7,10-tetraazacyclododecane.

33 g of the compound obtained in f or g are suspended in 80 cm³ of 98% sulphuric acid and heated at 100° C. in an argon atmosphere for 72 h. After being cooled, the reaction mixture is added dropwise to 1 l of ethyl ether at 0° C. The sulphate of 2,6-dimethyl-1,4,7,10-tetraazacyclododecane obtained is filtered off, taken up in water, neutralised with sodium hydroxide, then extracted with $CH_2Cl_2$. The organic phases are combined and evaporated to dryness, and the resulting 6 g of solid are used without further purification (yield 75%; Rf=0.65 aluminia/butanol/water/acetic acid/50/25/11).

NMR spectrum ($D_2O$): 6H $CH_3$(doublet 0.9 to 1 ppm); 14H $CH_2$ and CH (multiplet centred on 2.5 ppm).

i) Preparation of 2,6-dimethyl-1,4,7,10-tetraazacyclododecane-N,N',N'',N'''-tetraacetic acid.

A mixture of 5.7 g (60 mmoles) of monochloroacetic acid and 3.4 g (60 mmoles) in 25 cm³ of water is added to a solution of 3 g (15 mmoles) of the compound obtained in h in 25 cm³ of water. The mixture obtained is heated to 60° C. and a solution of potassium hydroxide (3.4 g, 60 mole in 25 cm³ of water is added so that the pH is maintained between 9 and 10. The addition requires 8 h. After the addition of potassium hydroxide is complete, heating is maintained for 24 h. After cooling, the pH is brought to 2.5 with concentrated HCl. The precipitate formed is filtered off, washed with ice-cold water and weighs 3 g after being dried (yield 35%; Rf=0.33 silica/ethyl acetate/isopropanol/ammonia/12/35/30). This compound corresponds to the complex of 2,6-dimethyl-1,4,7,10-tetraazacyclododecane-N,N',N'',N'''-tetraacetic acid with 2 KCl.

9.5 g of this complex are eluted with 200 cm$^3$ of 10% acetic acid from an ion exchange resin IRA 958 (OH) which has been regenerated beforehand with 1N NaOH and washed with water until it became neutral. The fractions obtained are evaporated to dryness and taken up 3 times in 50 cm$^3$ of water in order to eliminate traces of acetic acid. The residue obtained is triturated with ethyl ether (100 cm$^3$) to give, after filtration and drying, 6.3 g of a white solid. Yield: 89%.

NMR spectrum: (D$_2$O) 6H CH$_3$ (doublet 1.4 and 1.5 ppm); 14H CH$_2$ and CH (complex multiplet centred on 3.6 ppm); 8H CH$_2$COOH (doublet at 3.8 ppm).

EXAMPLE 2: Preparation of the gadolinium complex of 2,6-dimethyl-1,4,7,10-tetraazacyclododecane-N,N',N'',N'''-tetraacetic acid (methylglucamine salt)

Suspension of 5.425 g (12.54 mmole) of 2,6-dimethyl-1,4,7,10-tetraazacyclododecane-N,N',N'',N'''-tetraacetic acid obtained in example 1 i and 2.27 g of Gd$_2$O$_3$ (6.27 mmole) in 125 cm$^3$ of water is heated at 65° C. for 24 h. The pH is then adjusted to 7.4 by the addition of methylglucamine. After determination of free Gd$^{3+}$ by the xylenol orange/EDTA method, 650 mg of 2,6-dimethyl-1,4,7,10-tetraazacyclododecane-N,N',N'',N'''-tetraacetic acid (1.5 mmole) are added to complex the remaining gadolinium. The completion of complexation is confirmed by the absence of free Gd$^{3+}$ (determination with xylenol orange) and of free ligands (complexometric determination with Cu$^{2+}$). The determination of total gadolinium in the solution is carried out by atomic emission spectroscopy in DCP on a Spectrospan 4 Beckmann apparatus. Quantitative yield Rf=0.49 silica/ethyl acetate/isopropanol/ammonia/12/35/30).

EXAMPLE 3: Preparation of 2-hexyl-1,4,7,10-tetraazacyclododecane-N,N',N'',N'''-tetraacetic acid a) Preparation of N-(2-hydroxyethyl)-N-(2-hexyl-2-hydroxyethyl)amine.

50 g (0.39 mmole) of 1,2-epoxy-octane are added dropwise to 250 cm$^3$ (4 moles) of ethanolamine at 100° C. Heating is maintained for 1 h after the addition is complete, then the excess ethanolamine is distilled in a vacuum. The residue is recrystallised from 600 cm$^3$ of hexane, after filtration and drying. The solid residue obtained weighs 69 g (melting point 45° C., yield=93% Rf=0.62 silica/butanol/H$_2$O/acetic acid/50/25/11).

NMR spectrum: 3H CH$_3$ (triplet 0.9 ppm); 10H CH$_2$ chain (large singlet at 2.2 ppm); 7H CH$_2$ and CH (2 badly resolved masses at 2.8 and 3.8 ppm).

b) Preparation of N-tosyl-N-(2-tosyloxyethyl)-N-(2-hexyl-2-tosyloxyethyl amine.

47.3 g (0.25 mole) of the compound obtained in a are added in small portions to a solution of 156 g (0.82 mole) of tosyl chloride in 300 cm$^3$ of pyridine at 0° C. during 1 h. The mixture is maintained at 0° C. for 2 days, then it is poured into an ice/HCl mixture (2/1). The product is extracted with CH$_2$Cl$_2$, then chromatographed on a column of silica with CH$_2$Cl$_2$ as eluant. The mass obtained is 118 g (yield 72%; Rf=0.6 silica/CH$_2$Cl$_2$/acetone/98/2).

NMR spectrum: 3H CH$_3$ chain (triplet at 0.9 ppm); 10H CH$_2$ chain (large singlet at 1.3 ppm) 9H CH$_3$ tosyl (singlet at 2.4 ppm); 4H CH$_2$N (poorly resolved triplet at 3.4 ppm). 3H CH$_2$O and CH (multiplet at 4.2 ppm); 12H aromatics (multiplet between 7 and 7.7 ppm).

c) Preparation of N-tosyl-N-(2-azido-ethyl)-N-(2-hexyl-2-azidoethyl) amine.

87 g (0.133 mole) of the compound obtained in b and 29.25 g (0.5 mole) of sodium azide are mixed with 350 cm$^3$ of acetonitrile and 80 cm$^3$ of water. The mixture is heated at 65° C. for 3 days. The acetonitrile is then evaporated in a vacuum, the residue is taken up in CH$_2$Cl$_2$; the organic phase is washed with water, dried and evaporated; 50% of a yellow oil are recovered and used without purification (yield: 95%; Rf=0.75 silica/CH$_2$Cl$_2$/acetone/98/2).

NMR spectrum: 3H CH$_3$ chain (triplet at 0.9 ppm); 10H CH$_2$ chain (multiplet at 1.4 ppm); 3H CH$_3$ tosyl (singlet at 2.4 ppm); 5H CH$_2$ and CH (complex multiplet at 3.4 ppm); 4H aromatics (multiplet between 7.1 and 7.7 ppm).

I.R. spectrum N$_3$=2100 cm$^{-1}$ intense.

d) Preparation of N-tosyl-N(2-aminoethyl)-N-(2-hexyl-2-aminoethyl)amine 71 g (0.18 mole) of the diazide obtained in c are dissolved in 500 cm$^3$ of ethanol to which 5 g of palladium on charcoal at 50% humidity has been added. The suspension is stirred very vigorously under a stream of hydrogen at ambient temperature for 24 h. The catalyst is removed by filtration; after evaporation of the ethanol, 61.5 g of diamine are recovered and used without purification (yield: quantitative; Rf=0.51 silica/MeOH: NH$_4$OH/95/5).

e) Preparation of N-tosyl-N(2-tosylaminoethyl)-N-(2-hexyl-2-tosylaminoethyl)amine.

68.6 g (0.36 mole) of tosyl chloride are added in portions to a solution of 61.5 g (0.18 mole) of the compound obtained in d in 500 cm$^3$ of CH$_2$Cl$_2$ and 52.5 cm$^3$ (0.38 mole) of triethylamine at 0° C. After being stirred for 2 h at ambient temperature, the reaction mixture is treated with 500 cm$^3$ of water. The organic phase is washed with water, dried, evaporated; the oily residue is chromatographed on a column of silica with CH$_2$Cl$_2$ as eluant. The oil obtained after evaporation of the solvent and being taken up in isopropyl ether gives 60 g of white solid (melting point 120° C.; yield 51%; Rf=0.6 silica/CH$_2$Cl$_2$/MeOH/98/2).

NMR spectrum: 13H chain (poorly resolved multiplet centred at 1 ppm); 9H CH$_3$ tosyl (singlet at 2.4 ppm); 7H CH$_2$ and CH (multiplet centred at 3.1 ppm).

f) Preparation of N, N', N'', N'''-tetratosyl-2-hexyl-1,4,7,10-tetraazacyclododecane A mixture of 46.5 g (71.5 mmole) of the compound obtained in d above, 41.5 g (73 mmole) of the compound obtained in example 1 e and 24 g (70 mmole) of tetrabutylammonium hydrogen sulphate are suspended in 400 cm$^3$ of toluene and 200 cm$^3$ of 20% sodium hydroxide. The mixture is stirred very vigorously at 70° C. for 24 h. After cooling, the organic phase is washed with water, dried and evaporated. The residue is crystallised in ethanol, then chromatographed on a column of silica with CH$_2$Cl$_2$ as eluent. 35 g of solid are obtained (melting point 154°/161° C.). Yield 56%; Rf=0.55 silica/CH$_2$Cl$_2$/acetone/98/2.

NMR spectrum: 3H CH$_3$ chain (triplet at 0.9 ppm); 10H CH$_2$ chain (multiplet at 1.3 ppm); 12H CH$_3$ tosyl (singlet at 2.4 ppm); 15H CH$_2$ and CH ring (multiplet at 3.3 ppm); 16H aromatics (multiplet between 7.1 and 7.7 ppm).

g) Preparation of 2-hexyl-1,4,7,10-tetraazacyclododecane 12 g (13 mmoles) of the compound obtained in f are heated at 100° C. in 40 cm³ of 98% sulphuric acid under argon for 24 h. After being cooled, the mixture is added dropwise to 500 ml of ethyl ether at 0° C. The sulphate obtained is filtered, then neutralised by a 10% solution of sodium hydroxide and extracted with CH$_2$Cl$_2$. The organic phase is dried over sodium sulphate, then evaporated to dryness to give 2 g of a cream solid (yield: 57%; Rf=0.75 alumina/butanol/water/acetic acid/50/25/11).

The compound is stored in the form of the oxalate by reacting an ethanolic solution of oxalic acid with 2-hexyl-1,4,7,10-tetraazacyclododecane overnight at ambient temperature. The oxalate precipitates in the form of a white solid.

h) Preparation of 2-hexyl-1,4,7,10-tetraazacyclododecane-N, N', N'', N'''-tetraacetic acid.

A solution of 1.09 g (2.8 mmoles) of the oxalate obtained in g in 13 cm³ of water and 20 ml of ethanol is neutralised with 470 mg (8.4 mmoles) of potassium hydroxide. To this solution is added potassium monochloroacetate prepared from 1.063 g (11.25 mmoles) of monochloroacetic acid and 630 mg (11.25 mmoles) of potassium hydroxide in 20 cm³ of water. The reaction mixture is heated to 60° C. and the pH is maintained between 8 and 10 by the addition of potassium hydroxide. The addition requires 3 h during which 10 cm³ of water containing 630 mg of potassium hydroxide are added. After a reaction time of 3 h, 141 mg (1.5 mmoles) of chloroacetic acid and 84 mg (1.5 mmoles) of potassium hydroxide are added.

The mixture is then maintained at 60° C. for 2 days. After being cooled and acidified to pH 2.5 (6N HCl) the solution is passed through a column of a strongly basic resin IRA 958. Elution with 100 cm³ of 10% formic acid yields 700 mg of product. The flow-through fractions (product not retained) are concentrated and retreated on an identical column. After the same treatment, 2.5 g of product are recovered (yield: 38.4%; Rf=0.65 silica/ethanol/buffer/2/1).

NMR spectrum: 3H CH$_3$ chain (triplet 0.9 ppm); 10H CH$_2$ chain (multiplet at 1.4 ppm); 15H CH$_2$ and CH ring (multiplet at 2.3 ppm); 8H CH$_2$ COOH (singlet at 3.9 ppm). Spectrum carried out in D$_2$O.

EXAMPLE 4: Preparation of the gadolinium complex of 2-hexyl-1,4,7,10-tetraazacyclododecane-N, N', N'', N'''-tetraacetic acid 488.6 mg (1 mmole) of the compound obtained in example 3 and 181.3 mg (1 meq of metal) of gadolinium oxide are suspended in 40 cm³ of water and heated at 65° C. for 2 days. After 2 hours the solution is clear. The progress of the complexation is monitored during the reaction by determination of free gadolinium. When it is complete, the solution is filtered through a Millipore filter paper, then evaporated to dryness and crystallised from ethyl ether. 550 mg of white solid are thus recovered (yield: 85.5%; RF=0.65 EtOH/buffer/2/1).

EXAMPLE 5: Preparation of the gadolinium complex of 2-hexyl-1,4,7,10-tetraazacyclododecane-N, N', N'', N'''-tetraacetic acid (methylglucamine salt)

488.6 mg (1 mmole) of the compound obtained in example 3 and 181.3 mg (1 meq of metal) of gadolinium oxide are suspended in 40 cm³ of water and heated to 65° C. for 12 h. Methylglucamine is added to the clear solution to bring the pH to 7.4. Additions of ligands are made depending on the results of the analyses. The completion of complexation is confirmed by the absence of Gd$^{3+}$ (determination by xylenol orange) and of free ligands (complexometric determination with copper). The determination of total gadolinium in the solution is carried out by means of atomic emission spectroscopy on a Spectrospan 4 Beckmann apparatus. Rf=0.65 in EtOH/buffer/2/1.

EXAMPLE 6: Preparation of 2-methyl-1,4,7,10-tetraazacyclododecane-N, N', N'', N'''-tetraacetic acid a) Preparation of N, N'-ditosyl-1,2-diaminopropane.

In a 1 l 3-necked flask fitted with a magnetic stirrer, a thermometer and a guard tube, 14.8 g of 1,2-diaminopropane are dissolved in 500 ml of CH$_2$Cl$_2$ and 58 cm³ of Et$_3$N.

80 g of tosyl chloride are introduced in portions during 1 hour. Cooling in an ice bath is necessary in order to maintain a temperature of 20° C.

The reaction mixture is then stirred overnight at room temperature.

The reaction mixture is transferred to a 1 l separating funnel and then washed with 2×260 cm³ of water.

The organic fraction is dried over Na$_2$SO$_4$, evaporated to dryness, then crystallised from isopropyl ether.

| | |
|---|---|
| Weight obtained = | 66 g |
| Yield = | 86% |
| Melting point = | 98/100° C. |
| NMR | |
| 1 ppm doublet (3H) | 3.1 ppm multiplet (1H) |
| 2.4 ppm singlet (6H) | 5.5 ppm exchangeable singlet (2H) |
| 2.9 ppm doublet (2H) | 7.1 to 7.8 ppm aromatics (8H) |
| TLC | |
| SiO$_2$ eluant CH$_2$Cl$_2$ 90 | |
| MeOH 10 Rf = 0.75. | | b) Preparation of N, N'-ditosyl-bis (2-tosyloxyethyl) ethylene diamine.

In a 500 cm³ 3-necked flask fitted with a thermometer, a guard tube and a magnetic stirrer a solution of 162 g of tosyl chloride in 300 ml of pyridine is cooled to 0° C. by means of an ice-salt bath.

29.6 g of this (2-hydroxyethyl) ethylene diamine are added in portions during 2 h at this temperature. At no time must the temperature exceed 5° C. The reaction mixture is stirred for 4 h at this temperature, left for 48 h at 6°/8° C. in the refrigerator and then for 4 h at room temperature.

The reaction mixture is poured into 1 l of ice plus water and 300 ml of concentrated HCl. The product is extracted with 500 ml of CH$_2$Cl$_2$. This organic phase is dried over Na$_2$SO$_4$, then evaporated to dryness. The residue is taken up in 250 cm³ of ethanol by warming. The product crystallises. It is filtered off on a glass frit and dried at 60° C. for 48 h.

| | |
|---|---|
| Weight obtained = | 107.5 g |
| Yield = | 70% |
| Melting point = | 138/140° C. |
| NMR | |
| 2.4 ppm singlet (12H) | |
| 3.3 ppm singlet + triplet (8H) | |

| |
|---|
| 4.2 ppm triplet (4H) |
| 7.2 to 7.8 ppm multiplet (16H) |
| TLC |
| SiO₂ plate eluant toluene 80 Rf = 0.6 |
| acetone 20 | c) Preparation of N, N', N'', N'''-tetratosyl-2-methyl-1,4,7,10-tetraazacyclododecane In a 1 l 3-necked flask, a solution of 17.5 g of N, N' ditosyldiamino 1,2-propane in 500 ml of dry DMF is stirred for ½ hour at ambient temperature. 33 g of $Cs_2CO_3$ are powdered and added in suspension to this solution. This suspension is heated to 55° C. by means of an oil bath in an inert atmosphere.

A solution of 35 g of N, N'-ditosyl-bis (2-tosyloxyethyl) ethylene diamine in 200 cm³ of DMF is added dropwise at this temperature during 2 h. After the addition is complete, heating is continued for 48 h. The DMF is then removed by distillation in a vacuum. The residue is taken up in a water/$CH_2Cl_2$ mixture.

The organic phase is dried over $Na_2SO_4$. The solvent is removed by distillation in a rotary evaporator.

The residue is heated and stirred in 200 ml of ethyl acetate. The expected product crystallises. It is filtered off, then dried at 60° C. in a vacuum for 24 h.

| | |
|---|---|
| Weight obtained = | 22.5 g |
| Yield = | 61% |
| Melting point = | 274/275° C. |
| NMR | |
| 1 ppm doublet (2H) | |
| 2.2 ppm singlet (12H) | |
| 3 to 3.8 ppm multiplet (15H) | |
| 7.2 to 7.9 ppm multiplet (16H) aromatics | |
| TLC | |
| SiO₂ eluant toluene = | 80 |
| acetone = | 20 Rf = 0.56 | d) Preparation of 2-methyl-1,4,7,10-tetraazacyclododecane

In a 1 l 3-necked flask fitted with a thermometer, a balloon of argon and a mechanical stirrer, a solution of 72.5 g of the compound obtained in c) in 300 ml of 98% $H_2SO_4$ is heated at 100° C. for 48 h by means of an oil bath in an inert atmosphere.

The reaction mixture is cooled to ambient temperature and 800 ml of $Et_2O$, cooled to 0° C. by means of a bath of ethylene glycol and Dry Ice, is added during 1 h.

The very hygroscopic sulphate precipitates. It is filtered off carefully on a glass frit under nitrogen, then quickly dissolved in 200 ml of water. This solution is made alkaline (pellets of NaOH), then extracted with 5×100 ml of $CH_2Cl_2$.

The combined organic phases are dried over $Na_2SO_4$, then evaporated to dryness to give 15 g of very viscous crude product which crystallises on standing.

| |
|---|
| NMR |
| CDCl₃ 1.1 ppm doublet (2H) |
| Spectrum in +D₂O 2.7 ppm 2 singlets |
| as a multiplet (19H, 4 of which are exchangeable) |
| TLC |
| Al₂O₃ plate eluant BuOH 50 Rf = 0.8 |
| H₂O 25 |
| AcOH 11 | e) Preparation of the complex of 2-methyl-1,4,7,10-tetraazacyclododecane-N, N', N'', N'''-tetraacetic acid with 2 KCl.

In a 250 ml 3-necked flask a solution of 34 g of chloroacetic acid in 150 cm³ of water is cooled to 10° C. in an ice bath. 20 g of potassium hydroxide are added at this temperature to neutralise the acid.

The compound obtained in d is then dissolved in this solution. The reaction mixture is then heated to 65° C. by means of an oil bath.

A solution of 20 g of KOH in 50 cm³ of water is added cautiously during 6 h at this temperature while the pH is maintained between 8 and 10.

Heating is then continued for 72 hours, then the reaction mixture is acidified to pH=2.5 with concentrated HCl.

The complex precipitates. It is filtered off onto a glass frit, rinsed with 50 cm³ of water, then dried at 60° C. for 18 h in an oven.

Weight obtained=30 g
Yield=66%
Melting point>300° C.

f) Purification of 2-methyl-1,4,7,10-tetraazacyclododecane-1,4,7,10-tetraacetic acid.

30 g of the complex obtained in e are suspended in the presence of 150 cm³ of IRA 958 resin, which has been regenerated beforehand.

After dissolution of the complex, this suspension is applied to the head of a column containing 150 cm³ of IRA 958 resin.

The elution is carried out by a 5% acetic acid solution in water.

The fractions containing the expected pure product are evaporated to dryness in order to remove the acetic acid completely.

| | |
|---|---|
| Weight obtained = | 18.4 g |
| Yield = | 89% |
| Acidity = | 100.3% (4 equivalents) titrated with 0.1 M NaOH. |
| TLC | |
| SiO₂ eluant AcOEt 12 Rf = | 0.36 |
| Isopropanol 35 | |
| NH₃, H₂O 30 | |
| FAB mass spectrum: mass peak at M + 1 = 419. | |

EXAMPLE 7: Preparation of a solution of the gadolinium complex of 2-methyl-1,4,7,10-tetraazacyclododecane-N, N', N'', N'''-tetraacetic acid (methylglucamine salt)

21 g (50 mmoles) of the compound obtained in example 6 and 9.05 g (25 mmoles) of gadolinium oxide are dissolved in 50 ml of twice-distilled, de-aerated water at 70° C. After one hour, dissolution is complete and the pH is close to 3. After cooling, the pH is adjusted to 7.3 with methyglucamine. The solution is adjusted to 100 ml and filtered through a Millipore membrane 0.22 μm. A solution having a Gd content of 0.5 mole/l is thus obtained. This solution has a viscosity at 20° C. of less than 4 mPa.s. (Free Gd not detected).

EXAMPLE 8:
2-hydroxymethyl-1,4,7,10-tetraazacyclododecane-4,7,10-triacetic acid a) Preparation of N, N'-ditosyl-2,3-diaminopropionic acid.

To a solution of 46 g of sodium hydroxide in 500 cm³ of water, 40 g of the monohydrochloride of 2,3-diaminopropionic acid are added with vigorous stirring. 200 cm³ of ethyl ether are added followed by 110.5 g of tosyl chloride in portion during 1 h. Stirring is maintained for 12 h, the precipitate formed is filtered off, then washed with water and ethyl ether. The solid obtained is suspended in 1 l of water, then acidified with 6N HCl. After filtration and washing with water and ethyl ether, the solid is dried for 24 h at 60° C. in a vacuum.

| | |
|---|---|
| Weight obtained = | 76 g |
| Yield = | 65% |
| Melting point = | 200–201° C. |
| TLC: $SiO_2$ $CH_2Cl_2$ 80/MeOH 20 | |
| Rf: 0.5 | |

NMR
2.4 ppm singlet 6H ($CH_3$ of the tosyl group)
2.8 ppm multiplet 3H ($CH_2$, CH of the diamino chain)
3.5 to 5 ppm extended multiplet 3H exchangeable with $D_2O$
7.2 to 7.8 ppm multiplet 8H aromatics.

b) Preparation of N, N'-ditosyl-2,3-diaminopropanol.

In a 2 l 3-necked flask, a suspension of 40 g of the compound obtained in b) in 600 cm³ of THF is stirred at 20° C. in an inert and anhydrous atmosphere. (argon).

A solution of 500 ml of 1M $BH_3$: THF is added in an inert atmosphere during ½ h. The temperature of the reaction mixture rises to 30° C. Stirring is continued for 48 h. Hydrolysis is carried out cautiously with 20 ml of water. The THF is removed by distillation in a vacuum. The residue is extracted with a water/ether mixture. The organic phase is washed with water, dried over $Na_2SO_4$, then evaporated to dryness. The residue is triturated with isopropyl ether until it crystallises. After filtration and drying 35 g of product are obtained.

| |
|---|
| Yield: 90% |
| Melting point: 126–127° C. |
| TLC: $SiO_2$ $CH_2Cl_2$ 90/MeOH 10 |
| Rf: 0.6 |

NMR
2.7 ppm singlet "$CH_3$" of tosyl (6H)
3 to 3.7 ppm multiplet (7H, 2 of which are exchangeable)
.6.9 ppm triplet, exchangeable alcoholic OH (1H)
7.3 to 7.9 ppm multiplet aromatics (8H)

c) Preparation of N, N', N'', N'''-tetratosyl-2-hydroxymethyl-1,4,7,10-tetraazacyclododecane.

In a 2 l 3-necked flask under argon, 35 g of the compound obtained in b) are dissolved in 1 l of anhydrous DMF, then 58.6 g of anhydrous $Cs_2CO_3$ are added.

This suspension is stirred for 1 h at ambient temperature, then heated to 65° C. by means of an oil bath. A solution containing 69 g of N, N'-ditosyl-bis (2-tosyloxyethyl) ethylene diamine in 600 cm³ of anhydrous DMF are added dropwise at this temperature during 6 h. Heating at 65° C. is maintained overnight; the DMF is removed by distillation in a vacuum. The residue is taken up in a mixture of 400 ml of water and 400 cm³ of dichloromethane. The organic phase is decanted, washed with 200 cm³ of water, dried over $Na_2SO_4$, then evaporated to dryness. The residual oil is dissolved at 80° C. in 200 cm³ of toluene, then kept in the refrigerator for 48 h. for crystallisation to occur. 24 g of product are obtained. Yield: 32% Melting point: 143°–145° C. TLC: $SiO_2$ $CH_2Cl_2$ 90/AcOEt 10 Rf: 0.5 NMR 2.4 ppm singlet 12H $CH_3$ tosyl 3.2 to 4.1 ppm multiplet 17H $CH_2$ ring + $CH_2$-OH 7.2 to 8.1 ppm multiplet 16H aromatics d) Preparation of 2-hydroxymethyl-1,4,7,10-tetraazacyclododecane.

20 g of the compound obtained in c) are dissolved in 100 cm³ of 98% $H_2SO_4$. This solution is heated to 100° C. for 48 h in an inert atmosphere. The reaction mixture is cooled, then added dropwise to 1 l of ethyl ether cooled by means of a Dry Ice/acetone bath. The precipitate of the sulphate of the amine is filtered off onto a glass frit, then washed with ethyl ether. The solid is immediately dissolved in 200 cm³ of water, the solution is adjusted to pH 12 with NaOH, and evaporated to dryness. After drying the residual solid in a vacuum in the presence of $P_2O_5$, the product is extracted with $2\times100$ cm³ of refluxing (THF). Evaporation of the fractions obtained after extraction lead to a colourless oil. Weight obtained: 4.5 g of base Yield: 90% TLF: $Al_2O_3$ BuOH 50/Water 25/AcOH 11 Rf: 0.8 NMR ($CDCl_3$ spectrum) 2.8 ppm singlet (17H)+triplet 3.8 ppm exchangeable singlet (5H)

e) Preparation of 2-hydroxymethyl-1,4,7,10-tetraazacyclododecane-4,7,10-triacetic acid.

In a 250 cm³ 3-necked flask equipped with a heater-magnetic stirrer, a temperature probe and a pH electrode connected to an analog pH meter and a system for the addition of reagent correlated with the pH of the medium, a solution of 8.5 g of the compound obtained in d), 15.8 g of 2-chloroacetic acid and 100 ml of water is neutralised to pH=9.5 with the aid of a solution of 15.8 g of potassium hydroxide in 50 cm³ of water. The reaction mixture is then heated at 50° C. by means of an oil bath for 72 h. The pH is, moreover, continuously adjusted to 9.5 by the addition of a solution of potassium hydroxide. The mixture is cooled, acidified to pH=5, diluted with 500 cm³ and applied to a column of 500 cm³ of the strongly basic anion exchange resin IRA 958, which has been regenerated beforehand. The alkylation products bind to the resin. This latter is rinsed with water, then eluted with fractions of 5% acetic acid. The fractions are evaporated to dryness. The residue is a crude powder which is purified on a preparative HPLC column of diameter 40 loaded with RP.18-grafted silica. Weight obtained: 3.5 g of pure product Yield: 22% Melting point: 142°–144° C. TLC: $SiO_2$ AcOEt 12/Isopropanol 35/$NH_4OH$ 30 Rf: 0.35 Acidity: 198.7% (2 waves) Titration with 0.1M NaOH-corrected for $H_2O$ FAB mass spectrum: peak at M+1=377

EXAMPLE 9: Preparation of a solution of the gadolinium complex of 2-hydroxymethyl-1,4,7,10-tetraazacyclododecane-4,7,10-triacetic acid A suspension of 11.05 g of 2-hydroxymethyl-1,4,7,10-tetraazacyclododecane-4,7,10-triacetic acid and 5.07 g of gadolinium oxide in twice distilled water is heated at 80° C. for 1 h.

After cooling, the pH is adjusted to 7.3 by the addition of sodium hydroxide and the volume is adjusted to 100 ml. The determination of total gadolinium is carried out by atomic emission spectroscopy (0.2 Ml$^{-1}$).

EXAMPLE 10: Preparation of 2-hydroxymethyl-1,4,7,10-tetraazacyclododecane-1,4,7,10-tetraacetic acid In a reactor of 50 cm³ equipped with a magnetic stirrer, a solution of 0.7 g of 2-hydroxymethyl-1,4,7,10- tetraazacyclododecane-4,7,10-triacetic acid and 0.2 g of chloroacetic acid in 15 cm³ of water is heated at 70° C.

The pH is brought to 10.5 by means of a solution of potassium hydroxide and is maintained at this value for 48 h at 70° C.

When the reaction is complete, the pH is brought to 5, then the solution is applied to a IRA 958 resin.

The ligand is chromatographed on the resin by elution with 5% acetic acid.

After evaporation to dryness, the product is purified by preparative HPLC (RP18-grafted silica).

| TLC (silica) eluent ethyl acetate 12 Isopropanol 35 Rf = NH₃, H₂O 30 | 0.25 |
|---|---|
| FAB mass spectrum: peak at M + 1 = 435. | |

EXAMPLE 11: Preparation of 2-(2-hydroxymethyl)-1,4,7,10-tetraazacyladodecane-N, N', N", N'''-tetraacetic acid This ligand is prepared according to the procedure described in examples 8 and 10 for the synthesis of 2-hydroxymethyl-1,4,7,10-tetraazacyclododecane-N, N', N", N'''-tetraacetic acid starting from 3,4-diaminobutanoic acid (S. Kasina et al., J. Med Chem., 29, 1933, 1986).

EXAMPLE 12: Preparation of 2-methyl-1,4,7,10,13-pentaazacyclopentadecane-4,7,10,13-tetraacetic acid (product 12a) and 2-methyl-1,4,7,10,13-pentaazacyclopentadecane-1,4,7,10,13-pentaacetic acid (product 12b)

a) Preparation of 1,4,7,10,13-pentatosyl-2-methyl-1,4,7,10,13-pentaazacyclopentadecane.

35.7 g (0.093 mole) of N, N'-ditosyl-1,2-diaminopropane, 75.7 g of cesium carbonate (0.23 mole) and 800 ml of DMF are loaded into a 2 1 3-necked flask equipped with a coolant and a mechanical stirrer.

The mixture is placed under argon and heated at 75° C.

A solution of 83 g (0.012 mole) of 1,11-mesyloxy-3,6,9-tritosyl-3,6,9 triazaundecane synthesised according to Richman and Atkins, Organic Synthesis 58, p.86 in 700 ml of DMF is added during 4 hours at 75° C.

The reaction mixture is maintained at 75° C. for 48 hours, then is filtered and the filtrate is evaporated to dryness.

The residue is taken up in 700 ml of ethanol, the solid is filtered off then taken up in 800 ml of toluene by heating.

The solid is filtered off at room temperature, then dried at 60° C.

Weight obtained: 45.4 g Yield: 49% Analysis: TLC: SiO₂ 60 F 254 Merck Eluant CH₂Cl₂/Acetone 98.2 Rf 0.45 Mass spectrum DCI method (NH₃) Mass peak at 999.

b) Preparation of 2-methyl-1,4,7,10,13-pentaazacyclopentadecane.

44 g (0.044 mole) of the compound attained in a) are maintained for 72 hours at 100° C. in 130 ml of concentrated sulphuric acid.

After being cooled, the reaction mixture is poured into a mixture of 250 ml of ethyl ether and 250 ml of ethanol at 0° C.

The solid is filtered off, then dissolved in 250 ml of water and treated with carbon black. The solution is made alkaline with cesium hydroxide, then extracted with CH₂Cl₂. The organic solution is dried over Na₂SO₄ and evaporated to dryness. The amine thus obtained can be used as such or in the form of its hydrochloride.

Weight obtained: M=8.4 g as the free base M=13.2 g as the 5 HCl Yield: 72.8% Analysis of the hydrochloride: TLC: Al₂O₃ F 254 Merck Eluant: Ethanol/Isopropylamine 80/20 Developer: iodine Rf: 0.85 NMR: 1.7 ppm 3H CH₃ 3.7 ppm 19H CH₂ and CH.

c) Preparation of 2-methyl-1,4,7,10,13-pentaazacyclopentadecane-4,7,10,13-tetraacetic acid (product 12a) and 2-methyl-1,4,7,10,13-pentaazacyclopentadecane-1,4,7,10,13-pentaacetic acid (product 12b).

In a 500 ml 3-necked flask a solution of 25.7 g (0.27 mole) of chloroacetic acid in 50 ml of water is neutralised to pH=5 at T<10° C. by means of 5M potassium hydroxide.

10 g of the compound obtained in b) (10.043 mmole) dissolved in 20 ml of water are added to this solution. The mixture is heated at 55° C. and 50 ml of 5M potassium hydroxide are added during 48 hours to maintain a pH of 8.5–9.5. After the addition is complete, heating is maintained overnight. The reaction mixture is cooled and acidified to pH=3. The solution is then applied to 200 ml of DOWEX 50 W resin. Elution of the resin by means of 1 l of a 1M solution of ammonia leads to the recovery of 20 g of crude product. The crude product is dissolved in 150 ml of water and applied to 250 ml of IRA 958 resin. The resin is washed with water, then eluted with 2 l of 0.1M acetic acid, followed by 2 l of 0.8M acetic acid.

9 g of crude product 12a are obtained on evaporation of the 0.1M acetic acid. 2.5 g of crude product 12b are obtained on evaporation of the 0.8M acetic acid.

The products 12a and 12b are then purified by preparative HPLC on RP18-silica.

| Product obtained: | product 12a: | M = | 5 g |
|---|---|---|---|
| | product 12b: | M = | 1.1 g |

Yield: 30% Analysis: TLC: SiO₂ 60 F 254 Merck Eluant: ethyl acetate/isopropanol/NH₃ (30%)/12/35/30 Developer: iodine Product 12a Rf: 0.4 Product 12b Rf: 0.27 Water analysis: Product 12a: KF: 1.8% Product 12b: KF: 2.8% Acidity analysis by means of 0.1M NaOH Product 12a: 2 acidity analyses 98.6% and 100.6% titre: 99.6% Product 12b: 3 acidity determinations 199.2% and 92.4% titre: 97.3% FAB mass spectra: 12a peak at M+1 462 12b peak at M+1 520

EXAMPLE 13: Preparation of monopropionamide of 2-methyl-1,4,7,10-tetraazacyclododecane-N,N',N",N'''-tetraacetic acid 2-methyl-1,4,7,10-tetraazacyclododecane-N,N',N",N'''-tetraacetic acid (5 g; 0.0119 mole) is solubilized in 50 ml of water. To this solution are added 1.4 g (0.0119 mole) of dimethylaminopyridine and 0.7 g (0.0118 mole) of propylamine.

When the reaction mixture is homogeneous, 3.5 (0.0178 mole) of 1-ethyl-3-(3-dimethylaminopropyl)carbodiimide, hydrochloride (EDCI) are added portionwise. The pH is maintained between 4.5 and 5 during the first hour or reaction.

This solution is stirred at room temperature for 24 h. Then it is chromatographed on a column containing 80 cm³ of regenerated resin IRA 958. The elution is carried out with an aqueous 5% acetic acid solution.

The fractions containing the desired product and the unreacted starting material are evaporated to dryness in order to fully eliminate acetic acid.

After re-solution of the mixture in water, this mixture is passed through a column containing 100 cm³ of regenerated resin Dowex 1×8−400. The elution is carried out with water.

The fractions containing the desired product are evaporated to dryness.

| Acidity in aqueous alcoholic medium: | |
|---|---|
| 3 titrated functions | |
| 1 strong acidity | 97% |
| 2 weak acidities | 191% |
| TLC on SiO₂ | |
| Eluent ethyl acetate | 12 |
| isopropanol | 35 |
| NH₄OH | 30 |
| Rf = 0.5 | |

NMR (Brücker AC 200 E) TMS as internal reference, in DMSO: 0.83 ppm (t) $CH_3$; 0.96–1.08 ppm (m) 5H $CH_2$; 1.38–1.48 ppm (m) 2H $CH_2$; 2.5 ppm (s) 2H $CH_2$; 2.61–3.48 ppm (m) 21 H $CH_2$.

EXAMPLE 14: Preparation of a solution of the gadolinium complex of monopropionamide of 2-methyl-1,4,7,10-tetraazacyclododecane-N,N',N'',N'''-tetraacetic acid 50 mmoles of the compound obtained in Example 13 and 25 mmoles of gadolinium oxide are dissolved in 250 ml of twice-distilled, de-aerated water at 70° C. After one day, complexation is complete. The solution is filtered through a Millipore membrane 0.22 μm and evaporated up to the maximum concentration.

We claim:

1. A diagnostic composition which can be administered to man, comprising at least one complex formed by a gadolinium ion and a ligand of the formula Ib:

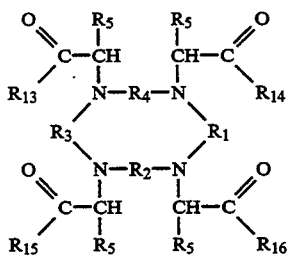

in which:

$R_1$ represents a radical of the formula

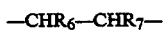
—CHR₆—CHR₇—

$R_6$ being selected from the group consisting of $C_1$–$C_{18}$ alkyl, $C_1$–$C_6$ hydroxyalkyl and $C_1$–$C_6$ polyhydroxyalkyl, $R_7$ being selected from the group consisting of hydrogen, $C_1$–$C_{14}$ alkyl, $C_1$–$C_6$ hydroxyalkyl, and $C_1$–$C_6$ polyhydroxyalkyl, $R_2$, $R_3$, $R_4$, identical or different, represent a radical of the formula

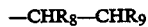
—CHR₈—CHR₉

$R_8$, $R_9$, identical or different, being selected from the group consisting of hydrogen, $C_1$–$C_{14}$ alkyl, $C_1$–$C_6$ hydroxyalkyl, and $C_1$–$C_6$ polyhydroxyalkyl, $R_5$ is selected from the group consisting of hydrogen, $C_1$–$C_{14}$ alkyl, $C_1$–$C_6$ hydroxyalkyl, and $C_1$–$C_6$ polyhydroxyalkyl, and $R_{13}$, $R_{14}$, $R_{15}$, $R_{16}$, identical or different, being selected from the group consisting of hydroxy and a group of the formula —NR₁₈R₁₇, $R_{17}$ and $R_{18}$, identical or different, being selected from the group consisting of hydrogen, $C_1$–$C_{14}$ alkyl, $C_1$–$C_6$ hydroxyalkyl, and $C_1$–$C_6$ polyhydroxyalkyl, as well as the salts thereof, with pharmaceutically acceptable mineral or organic bases or with basic amino acids.

2. The composition of claim 1 wherein the ligand is monopropionomide of 2-methyl-1,4,7,10-tetraazacyclododecane-N,N',N'',N'''-tetraacetic acid.

3. The composition of claim 1 wherein the ligand is monopropionomide of 2-methyl-1,4,7,10-tetraazacyclododecane-N,N',N'',N'''-tetraacetic acid, and the complex is a methylglucamine salt.

4. The composition of claim 1 wherein the ligand is 2,6-dimethyl-1,4,7,10-tetraazacyclododecane-N,N',N'',N'''-tetraacetic acid.

5. The composition of claim 1 wherein the ligand is 2-hexyl-1,4,7,10-tetraazacyclododecane-N,N',N'',N'''-tetraacetic acid.

6. The composition of claim 1 wherein the ligand is 2-hydroxymethyl-1,4,7,10-tetraazacyclododecane-4,7,10-triacetic acid.

7. The composition of claim 1 wherein the ligand is 2-hydroxymethyl-1,4,7,10-tetraazacyclododecane-1,4,7,10-tetraacetic acid.

8. The composition of claim 1 wherein the ligand is 2-hydroxyethyl-1,4,7,10-tetraazacyclododecane-1,4,7,10-tetraacetic acid.

9. The composition of claim 1 wherein the ligand is 2,6-dimethyl-1,4,7,10-tetraazacyclododecane-N,N',N'',N'''-tetraacetic acid, and the complex is a methylglucamine salt.

10. The composition of claim 1 wherein the ligand is 2-hexyl-1,4,7,10-tetraazacyclododecane-N,N',N'',N'''-tetraacetic acid, and the complex is a methyglucamine salt.

11. The composition of claim 1 wherein the ligand is 2-hydroxymethyl-1,4,7,10-tetraazacyclododecane-4,7,10-triacetic acid.

12. A method of obtaining an image by magnetic resonance comprising administering to a patient an effective amount of the composition of claim 1.

13. A method of obtaining an image by magnetic resonance comprising administering to a patient an effective amount of the composition of claim 2.

14. A method of obtaining an image by magnetic resonance comprising administering to a patient an effective amount of the composition of claim 3.

15. A method of obtaining an image by magnetic resonance comprising administering to a patient an effective amount of the composition of claim 4.

16. A method of obtaining an image by magnetic resonance comprising administering to a patient an effective amount of the composition of claim 5.

17. A method of obtaining an image by magnetic resonance comprising administering to a patient an effective amount of the composition of claim 6.

18. A method of obtaining an image by magnetic resonance comprising administering to a patient an effective amount of the composition of claim 7.

19. A method of obtaining an image by magnetic resonance comprising administering to a patient an effective amount of the composition of claim 8.

20. A method of obtaining an image by magnetic resonance comprising administering to a patient an effective amount of the composition of claim 9.

21. A method of obtaining an image by magnetic resonance comprising administering to a patient an effective amount of the composition of claim 10.

22. A method of obtaining an image by magnetic resonance comprising administering to a patient an effective amount of the composition of claim 11.

23. The composition of claim 1 constituted by a solution of the complex in an aqueous solvent.

24. The composition of claim 2 constituted by a solution of the complex in an aqueous solvent.

25. The composition of claim 3 constituted by a solution of the complex in an aqueous solvent.

26. The composition of claim 4 constituted by a solution of the complex in an aqueous solvent.

27. The composition of claim 5 constituted by a solution of the complex in an aqueous solvent.

28. The composition of claim 6 constituted by a solution of the complex in an aqueous solvent.

29. The composition of claim 7 constituted by a solution of the complex in an aqueous solvent.

30. The composition of claim 8 constituted by a solution of the complex in an aqueous solvent.

31. The composition of claim 9 constituted by a solution of the complex in an aqueous solvent.

32. The composition of claim 10 constituted by a solution of the complex in an aqueous solvent.

33. The composition of claim 11 constituted by a solution of the complex in an aqueous solvent.

* * * * *